(12) United States Patent
Schotland et al.

(10) Patent No.: US 6,618,463 B1
(45) Date of Patent: Sep. 9, 2003

(54) SYSTEM AND METHOD FOR SINGLE-BEAM INTERNAL REFLECTION TOMOGRAPHY

(75) Inventors: John Carl Schotland, Ladue, MO (US); Paul Scott Carney, Champaign, IL (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 10/191,666

(22) Filed: Jul. 9, 2002

(51) Int. Cl.[7] .................................................. H05G 1/00

(52) U.S. Cl. .............................. 378/21; 378/4; 378/901

(58) Field of Search ................................ 378/4, 15, 21, 378/22, 901

(56) References Cited

U.S. PATENT DOCUMENTS 6,441,356 B1 * 8/2002 Mandella et al. ........ 250/201.3

OTHER PUBLICATIONS

Fischer, "The information content of weakly scattered fields: implications for near–field imaging of three–dimensional structures", Journal of Modern Optics, vol. 47, No. 8, pp. 1359–1374, 2000.

* cited by examiner

Primary Examiner—David V. Bruce (57) ABSTRACT

A methodology and concomitant system for three-dimensional near-field microscopy achieves subwavelength resolution of an object via total internal reflection. The features of this approach include: (i) the evanescent waves used for illumination encode on the scattered field the subwavelength structure of the scattering object—it is thus possible to obtain subwavelength resolved images of the sample as is done in other near-field techniques such as near-field scanning optical microscopy without the technical difficulties encountered with probe-sample interactions; and (ii) the results of the reconstruction are unambiguous in the sense that the relation between the scattered field and the three-dimensional structure of the sample, as described by the spatial dependence of the susceptibility, is made manifest.

12 Claims, 4 Drawing Sheets

SYSTEM AND METHOD FOR SINGLE-BEAM INTERNAL REFLECTION TOMOGRAPHY

BACKGROUND OF THE DISCLOSURE

1. Field of the Invention

This invention relates to tomography and, more particularly, to tomography wherein an image of an object is directly reconstructed with sub-wavelength resolution.

2. Description of the Background Art

Total internal reflection microscopy (TIRM) brings to conventional microscopy the added functionality of illumination by evanescent waves. Incorporation of evanescent waves in the illuminating field is an important development for several reasons. First, the exponential decay of such waves along one direction allows for the control of the depth of penetration of the illuminating field. Second, evanescent waves may be used to resonantly excite surface plasmon modes of the sample. Finally, and perhaps most importantly, evanescent waves may be employed to supercede the Rayleigh diffraction limit of order half the wavelength, $\lambda/2$.

TIRM has been in practical use for decades. It has primarily been used as a surface inspection technique, though the sensitivity of the field to distance along the decay axis has been utilized to advantage in applications such as the measurement of distance between two surfaces. Until recently the opportunities for transverse superresolution made possible by the high spatial frequency content of the probe field have been largely over-looked. However, there have been advances in the realization of super-resolved imaging utilizing TIRM. There had been an initial direct imaging approach resulting from the marriage of standing-wave illumination techniques and TIRM achieving transverse resolution of $\lambda/7$. A later approach in which the information content of the TIRM experiment for the case of weakly-scattered fields has been determined is reported by Fischer in "The information content of weakly scattered fields: implications for near-field imaging of three-dimensional structures", published in Journal of Modern Optics, Vol. 47, No. 8, pages 1359–1374, 2000.

However, the art does not teach or suggest a technique for the reconstruction of a tomographic image of the object which is accomplished by making use of an analytic solution to an inverse scattering formulation with evanescent waves.

SUMMARY OF THE INVENTION

These shortcomings, as well as other limitations and deficiencies, are obviated in accordance with the present invention via a technique, referred to as total internal reflection tomography (TIRT,) whereby an object is probed with evanesent waves and then waves scattered from the object are processed with a prescribed mathematical algorithm to reconstruct the tomographic image.

In accordance with a broad method aspect of the present invention, a method for generating a tomographic image of an object includes: (1) probing the object with incident evanescent waves; (2) detecting waves scattered by the object, and (3) reconstructing the tomographic image of the object by executing a prescribed mathematical algorithm with reference to the incident evanescent waves and the scattered waves to generate the tomographic image with subwavelength spatial resolution.

A broad system aspect of the present invention is commensurate with the broad method aspect.

The features of the TIRT approach are at least three-fold: (i) the evanescent waves used for illumination encode on the scattered field the subwavelength structure of the scattering object. It is thus possible to obtain subwavelength resolved images of the sample as is done in other near-field techniques such as near-field scanning optical microscopy without the technical difficulties encountered with probe-sample interactions; and (ii) the results of the reconstruction are unambiguous in the sense that the relation between the scattered field and the three-dimensional structure of the sample, as described by the spatial dependence of the susceptibility, is made manifest. This is somewhat analogous to the transition from projection radiography to computed tomography.

DETAILED DESCRIPTION

1. Forward Problem

In this section we consider the scattering of evanescent waves from weakly-scattering dielectric media. In order to develop the physical ideas in a simple setting, we begin with the case of scalar waves. We then turn to the full vector theory of electromagnetic scattering thereby accounting for the effects of polarization. Note that the vector theory is essential since the scalar approximation to the scattering of electromagnetic waves is invalid when the dielectric susceptibility varies on subwavelength scales.

1.1 Scalar Case

Begin by considering an experiment in which a monochromatic scalar field is incident on a dielectric medium with susceptibility 72(r). The field incident on the sample will be taken to be an evanescent wave which is generated by total internal reflection at the interface of two half-spaces. One half-space, taken to be $z \geq 0$, will have the vacuum index of refraction 1 while the $z<0$ half-space will have an index of refraction n. The scalar field U(r) obeys the reduced wave equation $$\nabla^2 U(r)+k_0^2 n^2(z)U(r)=-4\pi k_0^2 \eta(r)U(r), \qquad (1)$$

where $k_0$ is the free-space wavenumber, n(z) is the z-dependent index of refraction as described above, and the support of $\eta(r)$ is contained in the $z \geq 0$ half-space. We represent the total field as the sum $$U=U_i+U_s, \qquad (2)$$

where $U_i$ and $U_s$ represent the incident and scattered fields, respectively. The incident field obeys the homogeneous equation $$\nabla^2 U_i(r)+k_0^2 n^2(z)U_i(r)=0. \qquad (3)$$

The scattered field obeys the equation $$\nabla^2 U_s(r)+k_0^2 n^2(z)U_s(r)=4\pi k_0^2 \eta(r)U(r). \qquad (4)$$

Equation (4) may be recast as the integral equation $$U_s(r)=k_0^2\int d^3r' G(r,r')U(r')\eta(r'), \qquad (5)$$

where $G(r,r')$ is the Green's function.

The Green's function $G(r,r')$ satisfies the equation $$\nabla^2 G(r,r')+n^2(z)k_0^2 G(r,r')=-4\pi\delta(r-r') \qquad (6)$$

and obeys the boundary conditions $$G(r,r')|_{z=0^+}=G(r,r')|_{z=0^-}, \qquad (7)$$

$$\hat{z}\cdot\nabla G(r,r')|_{z=0^+}=\hat{z}\cdot\nabla G(r,r')|_{z=0^-}. \qquad (8)$$

It may be seen that $G(r,r')$ admits the plane-wave decomposition $$G(r,r')=\frac{i}{2\pi}\int d^2q k_z^{-1}(q)\{1+R_1(q)\exp[2ik_z(q)z']\}\exp[ik(q)\cdot(r-r')], \qquad (9)$$

where $R_1(q)$ is the reflection coefficient given by $$R_1=\frac{k_z(q)-k'_z(q)}{k_z(q)+k'_z(q)}, \qquad (10)$$

with $$k_z(q)=\sqrt{k_0^2-q^2} \qquad (11)$$

$$k'_z(q)=\sqrt{n^2 k_0^2-q^2}, \qquad (12)$$

and $k(q)=(q, k_z(q))$. The plane wave modes appearing in Equation (7) are labeled by the transverse part of the wavevector q. The modes for which $|q|\leq k_0$ correspond to propagating waves while the modes with $|q|>k_0$ correspond to evanescent waves.

Figure 1:
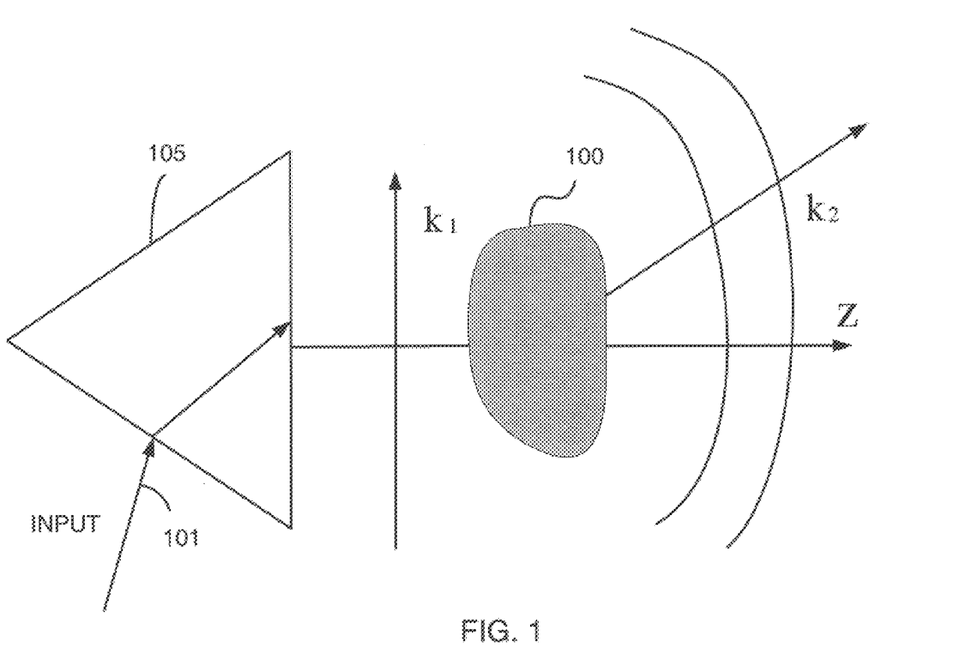
FIG. 1 illustrates a object/scatterer under test showing input evanescent waves generated at a prism face by total internal reflection an whereby the object scatters evanescent modes to the far zone.

Consider now the situation in which the incident field is an evanescent planewave of the form $$U_i(r)=\exp[ik(q)\cdot r], \qquad (13)$$

where q labels the transverse part of the incident wavevector. With reference to FIG. 1, if incoming wave 101 traverses prism 105 with index of refraction n, then $k_0\leq|q|\leq nk_0$. Thus $k_z$ is imaginary with the choice of sign dictated by the physical requirement that the field decay exponentially with increasing values of z. In the first Born approximation we replace the field by the incident field in the right hand side of equation (4) and obtain the following expression for the scattered field, which occurs because object 100 frustrates total internal reflection and scatters evanescent modes to the homogenous mode that propagates to the far field:

$$U_s(r)=k_0^2\int d^3r' G(r,r')U_i(r')\eta(r'). \qquad (14)$$

In the far zone of the scatterer, the leading term in the asymptotic expansion of the Green's function is given by the expression $$G(r,r')\sim\{1+R_1(q)\exp[2ik_z(q)z']\}\frac{\exp(ik_0 r)}{r}\exp[-ik(q)\cdot r'], \qquad (15)$$

where $k(q)$ is parallel to r and $|q|\leq k_0$. Using this result and equation (14) we find that the scattered field behaves as an outgoing homogeneous wave of the form $$U_s(r)\sim\frac{\exp(ik_0 r)}{r}A(q_1,q_2), \qquad (16)$$

where $q_1$ and $q_2$ are the transverse parts of the incident and outgoing wavevectors, respectively. Here $A(q_1,q_2)$, which is the scattering amplitude associated with the scattering of evanescent plane waves with transverse wavevector $q_1$ into homogeneous plane waves with transverse wavevector $q_2$, is related to the susceptibility of the scatting object by the expression $$A(q_1,q_2)=k_0^2\int d^3r\{1+R_1(q_2)\exp[2ik_z(q_2)z]\}\exp\{i[k(q_1)-k(q_2)]\cdot r\}\eta(r). \qquad (17)$$

We will take up the inversion of this integral equation in Section 2.1.

1.2 Vector Case

We now turn to the vector theory of electromagnetic scattering. As before, we consider an evanescent wave which is incident on a dielectric medium with susceptibility $\eta(r)$ and assume that the evanescent wave is produced at the interface of two half-spaces. We consider only nonmagnetic materials and accordingly will limit our attention to the electric field E which satisfies the reduced wave equation $$\nabla\times\nabla\times E(r)-k_0^2 n^2(z)E(r)=4\pi k_0^2\eta(r)E(r), \qquad (18)$$

where $k_0$ is the free space wave number and $n(z)$ is the background index of refraction as described in Section 1.1. We decompose the field into a sum of two parts, $$E=E^i+E^s. \qquad (19)$$

The incident field $E^i$ obeys the homogeneous equation $$\nabla\times\nabla\times E^i(r)-k_0^2 n^2(z)E^i(r)=0. \qquad (20)$$

The scattered field $E^s$ obeys $$\nabla\times\nabla\times E^s(r)-k_0^2 n^2(z)E^s(r)=4\pi k_0^2\eta(r)E(r). \qquad (21)$$

Equation (21) may be reformulated as the integral equation $$E_\alpha^s(r)=k_0^2\int d^3r' G_{\alpha\beta}(r,r')E_\beta(r')\eta(r), \qquad (22)$$

where $G_{\alpha\beta}(r,r')$ is the Green's tensor for the half-space and the summation convention over repeated indices applies and will throughout.

The Green's tensor $G_{\alpha\beta}(r,r')$ satisfies the equation $$\nabla\times\nabla\times G(r,r')-k_0^2 n^2(z)G(r,r')=4\pi\delta(r-r')I \qquad (23)$$

where I is the unit tensor. The Green's tensor must also satisfy the boundary conditions $$\hat{z}\times G(r,r')|_{z=0^+}=\hat{z}\times G(r,r')|_{z=0^-}, \qquad (24)$$

$$\hat{z}\times\nabla\times G(r,r')|_{z=0^+}=\hat{z}\times\nabla\times G(r,r')|_{z=0^-}. \qquad (25)$$

Making use of a planewave decomposition, it may be found that $$G_{\alpha\beta}(r,r') = \frac{i}{2\pi}\int \frac{d^2q}{k_z(q)} S_{\alpha\gamma}^{-1}(q) g_{\gamma\delta}(q,z) S_{\delta\beta}(q) \exp[ik(q)\cdot(r-r')], \quad (26)$$

where it is assumed that z>z'>0. Here the matrix S(q) rotates k(q) into the xz plane, or more explicitly $$S(q) = |q|^{-1}\begin{pmatrix} q_x & q_y & 0 \\ -q_y & q_x & 0 \\ 0 & 0 & |q| \end{pmatrix} \quad (27)$$

$$g_{xx} = \left(\frac{k_z(q)}{k_0}\right)^2 \{1 + R_2(q)\exp[2ik_z(q)z']\}, \quad (28)$$

$$g_{yy} = 1 + R_1(q)\exp[2ik_z(q)z'], \quad (29)$$

$$g_{zz} = \left(\frac{|q|}{k_0}\right)^2 \{1 - R_2(q)\exp[2ik_z(q)z']\}, \quad (30)$$

$$g_{zx} = \frac{-|q|k_z(q)}{k_0^2}\{1 + R_2(q)\exp[2ik_z(q)z']\}, \quad (31)$$

$$g_{xz} = \frac{-|q|k_z(q)}{k_0^2}\{1 - R_2(q)\exp[2ik_z(q)z']\}, \quad (32)$$

all other elements of g being zero, $R_1(q)$ is defined in equation (10), and $R_2(q)$ is given by $$R_2(q) = \frac{k_z'(q) - nk_z(q)}{k_z'(q) + nk_z(q)}. \quad (33)$$

We take the incident field to be an evanescent plane wave with polarization $E^{(0)}$ $$E_\alpha^i(r) = E_\alpha^{(0)}\exp[ik(q)\cdot r], \quad (34)$$

where k(q) is the incident wavevector and $k_0 \leq |q| \leq nk_0$. Within the accuracy of the first Born approximation, we find that the scattered field is given by the expression $$E_\alpha^s(r) = k_0^2 \int d^3r' G_{\alpha\beta}(r,r') E_\beta^{(0)} \exp[ik(q)\cdot r']\eta(r'). \quad (35)$$

In the far zone of the scatterer the Green's tensor assumes the asymptotic form $$G_{\alpha\beta}(r,r') \sim S_{\alpha\gamma}^\dagger(q) g_{\gamma\delta}(q,z) S_{\delta\beta}(q) \frac{\exp(ik_0 r)}{r} \exp[-ik(q)\cdot r'] \quad (36)$$

where k(q) lies in the direction of r. Thus we find that the sccattered field becomes $$E_\alpha^s(r) \sim A_{\alpha\beta}(q_1,q_2) E_\beta^{(0)} \frac{\exp(ik_0 r)}{r}, \quad (37)$$

where $q_1$ and $q_2$ are the transverse parts of the of the incident and outgoing wavevectors, respectively. $A_{\alpha\beta}(q_1,q_2)$ denotes the tensor scattering amplitude which is related to the susceptibility by $$A_{\alpha\beta}(q_1,q_2) = \int d^3r w_{\alpha\beta}(q_2,z) \exp\{i[k(q_1)-k(q_2)]\cdot r\}\eta(r), \quad (38)$$

where $$w_{\alpha\beta}(q,z) = k_0^2 S_{\alpha\gamma}^\dagger(q) g_{\gamma\delta}(q,z) S_{\delta\beta}(q). \quad (39)$$

Inversion of the above integral equation will be discussed in Section 2.2.

2. Inverse Problem

The inverse problem consists of reconstructing the susceptibility from measurements of the scattering amplitude. To this end we will construct the pseudoinverse solution of the integral equations (17) and (38). We begin by briefly reviewing the singular value decomposition (SVD) of linear operators on Hilbert spaces. Let A denote a linear operator with kernel A(x,y) which maps the Hilbert space $H_1$ into the Hilbert space $H_2$. By the SVD of A we mean a representation of the form $$A(x,y) = \sum_n \sigma_n g_n(x) f_n^*(y), \quad (40)$$

where $\sigma_n$ is the singular value associated with the singular functions $f_n$ and $g_n$. The $\{f_n\}$ and $\{g_n\}$ are orthonormal bases of $H_1$ and $H_2$, respectively and are eigenfunctions with eigenvalues $\sigma_n^2$ of the positive self-adjoint operators $A^*A$ and $AA^*$:

$$A^*Af_n = \sigma_n^2 f_n \quad (41)$$

$$AA^*g_n = \sigma_n^2 g_n. \quad (42)$$

In addition, the $f_n$ and $g_n$ are related by $$Af_n = \sigma_n g_n \quad (43)$$

$$A^*g_n = \sigma_n f_n. \quad (44)$$

The pseudoinverse solution to the equation Af=g is defined to be the minimizer of $\|Af-g\|$ with smallest norm. This well-defined element $f^+ \in N(A)^\perp$ is unique and may be shown to be of the form $f^+ = A^+g$, where the pseudoinverse operator $A^+$ is given by $A^+ = A^*(AA^*)^{-1}$ and $N(A)^{195}$ is the orthogonal complement of the null space of A. The SVD of A may be used to express $A^+$ as $$A^+(x,y) = \sum_n \frac{1}{\sigma_n} f_n(x) g_n^*(y). \quad (45)$$

We now apply the foregoing to the inverse problem for scalar waves.

2.1 Scalar Case

The integral equation (17) may be rewritten in the form $$A(q_1,q_2) = \int d^3r K(q_1,q_2;r)\eta(r), \quad (46)$$

where the scattering operator $K(q_1,q_2;r)$ is given by $$K(q_1,q_2;r) = \exp[i(q_1-q_2)\cdot\rho]\kappa(q_1,q_2;z), \quad (47)$$

with $$\kappa(q_1,q_2;z) = k_0^2\{1+R_1(q_2)\exp[2ik_z(q_2)z]\}\exp[i(k_z(q_1)-k_z(q_2))z]\chi(q_1,q_2). \quad (48)$$

Here we have assumed that $A(q_1,q_2)$ is measured for $(q_1,q_2)$, in the data set $Q$ and have introduced a function $\chi(q_1,q_2)$ which is unity if $(q_1,q_2) \in Q$ and is zero otherwise. Note that $Q$ specifies the available orientations of the incoming and outgoing wavevectors while $\chi(q_1,q_2)$ enforces the constraints $k_0 \leq |q_1| \leq nk_0$ and $|q_2| \leq k_0$. In general, the wavevectors $q_1$ and $q_2$ vary continuously over all space. If, however, the transverse support of $\eta(r)$ is contained in the region $[-L,L]\times[-L,L]$, then $q_1$ and $q_2$ may be taken to be discrete and restricted to the set $\Lambda=\{(n_x\pi/L, n_y\pi/L): n_x, n_y=0, \pm 1, \ldots\}$. Thus $\eta(r)$ may be expressed as the Fourier series $$\eta(\rho, z) = \sum_{q \in \Lambda} c_q(z)\exp(iq\cdot\rho), \quad (49)$$

where $c_q(z)$ are appropriate coefficients.

In order to obtain the SVD of $K(q_1, q_2; r)$ it will prove useful to introduce the following identity:

$$K(q_1, q_2; r) = \sum_{Q \in \Lambda} \exp(iQ\cdot\rho)\delta(Q+q_2-q_1)\kappa(Q+q_2, q_2; z), \quad (50)$$

where $\delta$ denotes the kronecker delta. Using this result, we find that the matrix elements of the operator $KK^*$ are given by $$KK^*(q_1, q_2; q_1', q_2') = \sum_{Q \in \Lambda} M(q_2, q_2'; Q)\delta(Q+q_2-q_1)\delta(Q+q_2'-q_1'), \quad (51)$$

where $$M(q_2, q_2'; Q) = \int_0^L dz\, \kappa(Q+q_2, q_2; z)\kappa^*(Q+q_2', q_2'; z), \quad (52)$$

with L the range of $\eta(r)$ in the $\hat{z}$ direction. To find the singular vectors $g_{QQ'}$ of K which satisfy $$KK^*g_{QQ'} = \sigma_{QQ'}^2 g_{QQ'}; \quad (53)$$

we will make the ansatz $$g_{QQ'}(q_1, q_2) = C_{Q'}(q_2; Q)\delta(Q+q_2-q_1), \quad (54)$$

where $Q, Q' \in \Lambda$. Equation (51) now implies that $$\sum_{q' \in \Lambda} M(q, q'; Q)C_{Q'}(q'; Q) = \sigma_{QQ'}^2 C_{Q'}(q; Q). \quad (55)$$

Thus $C_{Q'}(q_2; Q)$ is an eigenvector of $M(Q)$ labeled by $Q'$ with eigenvalue $\sigma_{QQ'}^2$. Since $M(Q)$ is self-adjoint, the $C_{Q'}(q_2; Q)$ may be taken to orthonormal. Next, the $f_{QQ'}$ may be found from $K^*g_{QQ'} = \sigma_{QQ'}f_{QQ'}$ and are given by $$f_{QQ'}(r) = \frac{1}{\sigma_{QQ'}}\sum_{q \in \Lambda} \exp(-iQ\cdot\rho)\kappa^*(Q+q, q; z)C_{Q'}(q; Q). \quad (56)$$

It follows that the SVD of $K(q_1, q_2; r)$ is given by the expression $$K(q_1, q_2; r) = \sum_{Q, Q'} \sigma_{QQ'} f_{QQ'}^*(r)g_{QQ'}(q_1, q_2). \quad (57)$$

The SVD of equation (57) may now be used to obtain the pseudoinverse solution to the integral equation (46):

$$\eta^+(r) = \sum_{q_1, q_2} K^+(r; q_1, q_2)A(q_1, q_2), \quad (58)$$

where $K^+(r; q_1, q_2)$ is the pseudoinverse of $K(q_1, q_2; r)$. Using the result of equation (45), the pseudoinverse $K^+$ may be seen to be given by $$K^+(r; q_1, q_2) = \sum_{Q, Q'} \frac{1}{\sigma_{QQ'}} f_{QQ'}(r)g_{QQ'}^*(q_1, q_2). \quad (59)$$

Substituting equations (54) and (56) into equation (59) and using the spectral decomposition $$\sum_{Q'} \frac{1}{\sigma_{QQ'}^2} C_{Q'}(q; Q)C_{Q'}^*(q'; Q) = M^{-1}(q, q'; Q), \quad (60)$$

where $M^{-1}(q, q'; Q)$ is the $qq'$ matrix element of $M^{-1}(Q)$ we obtain $$\eta^+(r) = \quad (61)$$
$$\sum_{q_1, q_2, q_2'} \sum_Q \exp(-iQ\cdot\rho)\delta(Q+q_2-q_1)M^{-1}(q_2, q_2'; Q) \times$$
$$\kappa^*(Q+q_2', q_2'; z)A(q_1, q_2),$$

which is the inversion formula for scalar TIRT.

2.2 Vector Case

The integral equation (38) may be rewritten in the form $$A_{\alpha\beta}(q_1, q_2) = \int d^3r K_{\alpha\beta}(q_1, q_2; r)\eta(r), \quad (62)$$

where the scattering operator $K_{\alpha\beta}(q_1, q_2; r)$ is given by $$K_{\alpha\beta}(q_1, q_2; r) = \exp[i(q_1-q_2)\cdot\rho]\kappa_{\alpha\beta}(q_1, q_2; z), \quad (63)$$

and $$\kappa_{\alpha\beta}(q_1, q_2; z) = w_{\alpha\beta}(q_2; z)\exp[i(k_z(q_1)-k_z(q_2))z]\chi(q_1, q_2). \quad (64)$$

As in the scalar case we have assumed that $A(q_1, q_2)$ is measured for $(q_1, q_2)$, in the data set $\mathcal{Q}$ and have introduced the appropriate blocking function $\chi(q_1, q_2)$. The vector integral equation (62) differs from its scalar counterpart equation (46) only by a factor associated with the polarization. Evidently, by measuring a fixed component of the scattered field for a particular incident direction we see that the scalar inversion formula (61) may be used to reconstruct $\eta(r)$.

We now consider the SVD for the vector case. This is a simple generalization of the scalar case. Following the previous development we find that the SVD of $K_{\alpha\beta}(q_1, q_2; r)$ is of the form $$K_{\alpha\beta}(q_1, q_2; r) = \sum_{Q, Q'} \sigma_{QQ'} f_{QQ'}^*(r) g_{QQ'}^{\alpha\beta}(q_1, q_2). \quad (65)$$

Here the singular functions are given by $$g_{QQ'}^{\alpha\beta}(q_1, q_2) = C_{Q'}^{\alpha\beta}(q_2; Q)\delta(Q+q_2-q_1), \quad (66)$$

$$f_{QQ'}(r) = \frac{1}{\sigma_{QQ'}}\sum_{q \in \Lambda}\exp(-iQ\cdot\rho)\kappa^*(Q+q, q; z)C_{Q'}^*(q; Q). \quad (67)$$

The $C_{Q'}^{\alpha\beta}(q_2; Q)$ are eigenfuntions of $M_{\alpha\beta}^{\alpha'\beta'}(q_2, q'_2; Q)$ with eigenvalues=$\sigma_{QQ'}^2$ $$\sum_{q' \in \Lambda} M_{\alpha\beta}^{\alpha'\beta'}(q, q'; Q) C_{Q'}^{\alpha'\beta'}(q'; Q) = \sigma_{QQ'}^2 C_{Q'}^{\alpha\beta}(q; Q), \quad (68)$$

where $$M_{\alpha\beta}^{\alpha'\beta'}(q_2, q'_2; Q) = \int_0^L dz \kappa_{\alpha\beta}(Q + q_2, q_2; z) \kappa_{\alpha'\beta'}^*(Q + q'_2, q'_2; z). \quad (69)$$

The pseudoinverse solution to the integral equation (62) is given by $$\eta^+(r) = \sum_{q_1, q_2} K_{\alpha\beta}^+(r; q_1, q_2) A_{\alpha\beta}(q_1, q_2), \quad (70)$$

where $$K_{\alpha\beta}^+(r; q_1, q_2) = \sum_{Q,Q'} \frac{1}{\sigma_{QQ'}} f_{QQ'}(r) g_{QQ'}^{\alpha\beta\,*}(q_1, q_2). \quad (71)$$

More explicitly, we have $$\eta^+(r) = \sum_{q_1, q_2, q'_2} \sum_Q \exp(-iQ \cdot \rho) \delta(Q + q_2 - q_1) \quad (72)$$

$$(M^{-1}(Q))_{\alpha\beta}^{\alpha'\beta'}(q_2, q'_2) \times \kappa_{\alpha'\beta'}^*(Q + q'_2, q'_2; z) A_{\alpha\beta}(q_1, q_2),$$

which is the inversion formula for vector TIRT.

3. Regularization

In order to avoid numerical instabilty and set the resolution of the reconstructed image to be comensurate with the available data, the SVD inversion formulas must be regularized. In particular, we replace 1/a in the inversion formulas (61) and (72) by $R(\sigma)$ where R is a suitable regularizer. where R is a suitable regularizer. The effect of regularization is to limit the contribution of the small singular values to the reconstruction. One way to do this is to simply cutoff all a below some cutoff $\sigma_c$. That is we set $$R(\sigma) = \frac{1}{\sigma^2} \theta(\sigma - \sigma_c), \quad (73)$$

θ denoting the usual Heavyside step function. Alternatively a smooth cutoff, such as that derived by the Tikhonov method, may be employed.

4. Example

To demonstrate the feasibility of the inversion using a scalar formalation, for simplicity, the reconstruction of $\eta(r)$ has been obtained for a collection of spherical scatterers. This collection is representative of physical structures which may be imaged, such as a nano-structured material; the collection presents the necessary dielectric contrast to effect direct reconstruction. The forward data was calculated by considering the scattering of evanescent waves from a homogeneous sphere including multiple scattering terms by means of a partial wave expansion. Consider a sphere of radius a centered at the point $r_0$ with refractive index n, n being related to the scattering potential or susceptibility by the expression $n^2 = 1 + 4\pi\eta$. It may be found that $$A(k_1, k_2) = \exp[i(k_1 - k_2) \cdot r_0] \sum_{l=0}^{\infty} (2l + 1) A_l P_l(\hat{k}_1 \cdot \hat{k}_2), \quad (74)$$

where $A_l$ are the usual partial wave expansion coefficients, $P_l$ are the Legendre polynomials, and $\hat{k} = k/\sqrt{k \cdot k^*}$. Since evanescent waves are considered, the argument of the Legendre polynomials in equation (74) may exceed unity. The series may nonetheless be shown to be convergent due to the rapid decay of the $A_l$ with increasing l.

The forward data was obtained for a collection of four spheres of radius $\lambda/20$. All scatterers are present simultaneously in the forward computation with inter-sphere scattering neglected. The incident evanescent waves were taken to have transverse wave vectors $q_1$ on a Cartesian grid with spacing $k_0/4$ such that $k_0 \leq |q| \leq nk_0$, n being the refractive index of the prism used to generate the incident waves. Values of $q_2$ were also taken on the grid with spacing $k_0/4$ and $|q_2| \leq k_0$, consistent with a measurement scheme in which the scattered field is measured in the far zone of the lower half-space. The spheres are arranged in two layers, one equatorial plane coninicident with the $z=\lambda/20$ plane, the other with the $z=\lambda/4$ plane. In each layer, one sphere was taken to have susceptibility $4\pi\eta=0.44$ (index n=1.2) and one sphere was taken to have susceptibility $4\pi\eta=0.4+0.48i$ (index n=1.1+0.2i). In each of the experiments, complex Gaussian noise of zero mean was added to the signal at various levels. The experiments were performed for two different prisms, namely, for FIG. 2A, the prism has an index of n=10, as might be encountered in the infrared range, and for FIG. 2B, an index n=4, as might be encountered in the visible range. The data sets are thus composed of 4980×49 points for the higher-index prism, and 752×49 data poins for the lower-index prism. The regularization parameter $\sigma_c$ was taken to be $10^{-6}$ in computing the tomographic image at z $\lambda/20$ and $10^{-5}$ at $z=\lambda/4$.

Figure 2A:
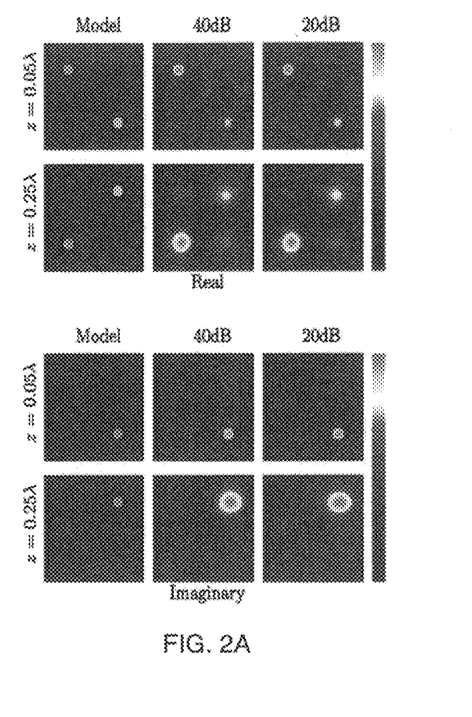
FIGS. 2A and 2B depict direct reconstruction results for an exemplary scatterer using different parameters.
Figure 2B:
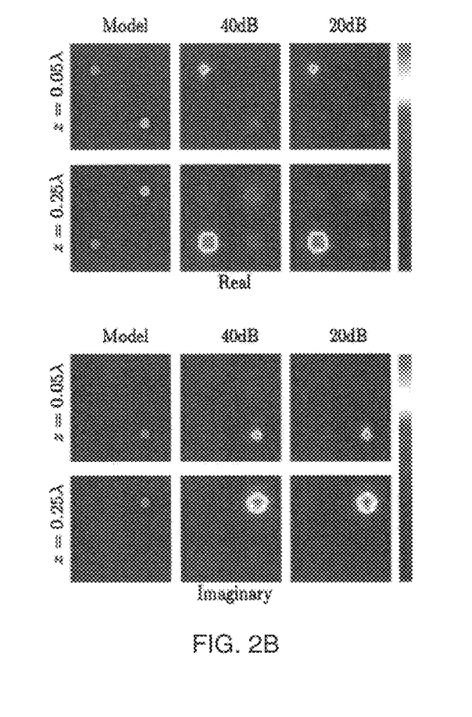

One can see from the reconstructions of FIGS. 2A and 2B that the real and imaginary parts of the susceptibility may be found separately and that the reconstructions are subwavelength resolved. The resolution depends both on the size of the regularization parameter, which indirectly sets the number of singular functions used in the reconstruction, and on the depth, a consequence of the fact that the probe fields decay exponentially into the sample, resulting in loss of high-frequency Fourier components of the spatial structure of the susceptibility. The tomographs at the $z=\lambda/20$ layer are more highly resolved for the higher-index prism than for the lower-index prism, but there is little difference at the $z=\lambda/4$ layer.

5. System

Figure 3:
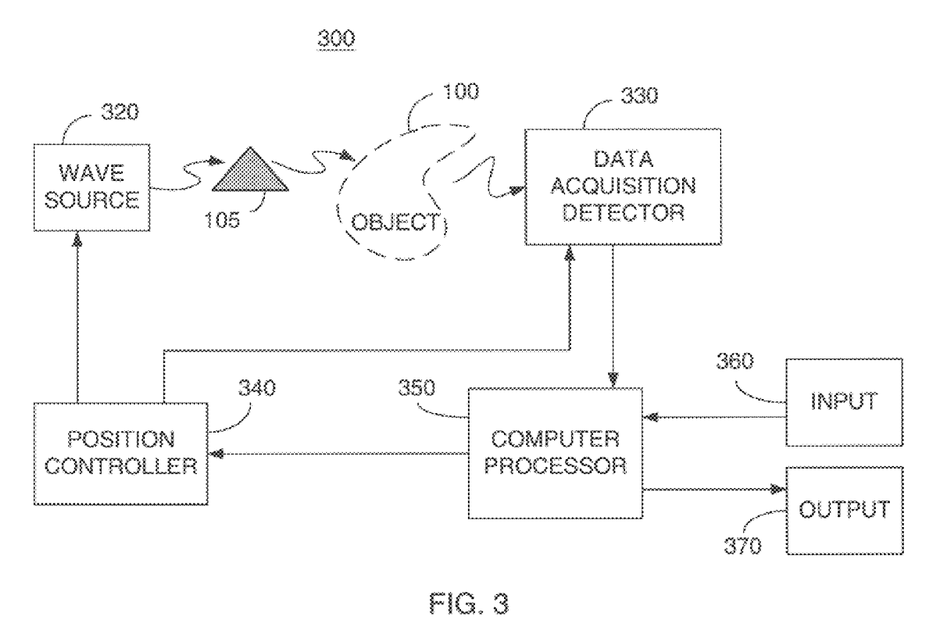
FIG. 3 is a high-level block diagram of a system for directly reconstructing the tomographic image of the scatterer.

As depicted in high-level block diagram form in FIG. 3, system 300 is a tomography system for generating an image of an scatterer/object using measurements of scattered waves emanating from an object in response to waves illuminating the object. In particular, object 100 is shown as being under investigation. System 300 is composed of: source 320 for probing the object 100 through prism 105; data acquisition detector 330 for detecting the scattering data corresponding to the scattered waves from object 100 at one or more locations proximate to object 100; position controller 340 for controlling the locations of detectors 330 and sources 320; and computer processor 350, having associated input device 360 (e.g., a keyboard) and output device 370

(e.g., a graphical display terminal). Computer processor 350 has as its inputs positional information from controller 340 and the measured scattering data from detector 330. Even though the scatterer is shown as being present in FIG. 3, actually two sets of measurements are obtained, namely, one set with the scatterer removed, and another set with the scatterer present, to provide the necessary data for image reconstruction, as detailed above.

Computer 350 stores a computer program which implements the direct reconstruction algorithm; in particular, the stored program processes the measured scattering data to produce the image of the object or object under study using a prescribed mathematical algorithm. The algorithm is, generally, determined with reference to an integral operator relating the scattering data to the forward scattering operator as expressed by integral equation (17) or equation (38).

6. Flow Diagram

Figure 4:
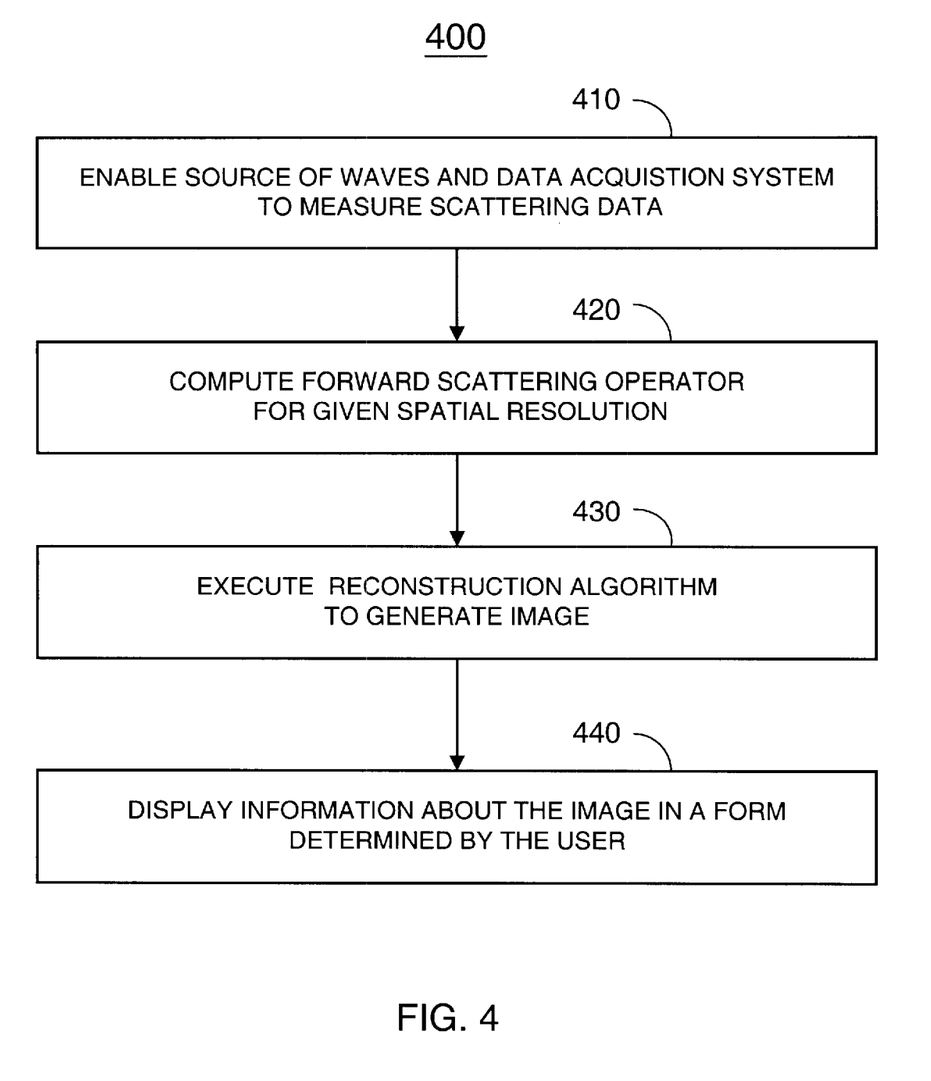
FIG. 4 is a flow diagram of the methodology for directly reconstructing the tomographic image of the scatterer.

The methodology carried out by the present invention is set forth in high-level flow diagram 400 of FIG. 4 in terms of the illustrative system embodiment shown in FIG. 3. With reference to FIG. 4, the processing effected by block 410 enables source 320 and data acquisition detector 330 so as to measure the scattering data emanating from scatterer 100 due to illuminating waves from source 320. These measurements are passed to computer processor 350 from data acquisition detector 330 via bus 331. Next, processing block 420 is invoked to compute the kernel expressed by equation (17) or equation (38), which may for efficiency be precomputed and stored. In turn, processing block 430 is operated to execute the reconstruction algorithm set forth in equation (17) or equation (38), thereby determining the scattering potential $\eta(r)$. Finally, as depicted by processing block 440, the reconstructed tomographic image corresponding to $\eta(r)$ is provided to output device 370 in a form determined by the user; device 370 may be, for example, a display monitor or a more sophisticated three-dimensional display device.

Although the present invention have been shown and described in detail herein, those skilled in the art can readily devise many other varied embodiments that still incorporate these teachings. Thus, the previous description merely illustrates the principles of the invention. It will thus be appreciated that those with ordinary skill in the art will be able to devise various arrangements which, although not explicitly described or shown herein, embody principles of the invention and are included within its spirit and scope. Furthermore, all examples and conditional language recited herein are principally intended expressly to be only for pedagogical purposes to aid the reader in understanding the principles of the invention and the concepts contributed by the inventor to furthering the art, and are to be construed as being without limitation to such specifically recited examples and conditions. Moreover, all statements herein reciting principles, aspects, and embodiments of the invention, as well as specific examples thereof, are intended to encompass both structural and functional equivalents thereof. Additionally, it is intended that such equivalents include both currently know equivalents as well as equivalents developed in the future, that is, any elements developed that perform the function, regardless of structure.

In addition, it will be appreciated by those with ordinary skill in the art that the block diagrams herein represent conceptual views of illustrative circuitry embodying the principles of the invention.

What is claimed is:

1. A method for generating a tomographic image of an object comprising:
    probing the object with incident evanescent waves,
    detecting waves scattered by the object, and
    reconstructing the tomographic image by executing a prescribed mathematical algorithm with reference to the incident waves and the scattered waves to generate the tomographic image with subwavelength resolution.

2. The method as recited in claim 1 wherein the detecting includes measuring scattering data from the object, said scattering data being related to a scattering potential of the object by an integral operator.

3. The method as recited in claim 2 wherein the reconstructing includes reconstructing the tomographic image by executing the prescribed mathematical algorithm, determined with reference to the integral operator, on the scattering data, the prescribed mathematical algorithm further relating the scattering potential to the scattering data by another integral operator.

4. The method as recited in claim 1 wherein the probing includes illuminating a prism to generate the incident waves.

5. A method for generating a tomographic image of an object comprising:
    illuminating the object with incident evanescent waves,
    measuring scattering data from the object wherein the scattering data is related to the object by an integral operator, and
    reconstructing the tomographic image by executing a prescribed mathematical algorithm, determined with reference to the integral operator, on the scattering data to generate the tomographic image with subwavelength resolution.

6. The method as recited in claim 5 wherein the scattering data is related to a scattering potential of the object by the integral operator, and wherein the reconstructing includes reconstructing the tomographic image by executing the prescribed mathematical algorithm, determined with reference to the integral operator, on the scattering data, the prescribed mathematical algorithm further relating the scattering potential to the scattering data by another integral operator.

7. The method as recited in claim 5 wherein the illuminating includes illuminating a prism to generate the incident waves.

8. A system for generating a tomographic image of an object comprising:
    a source for probing the object with incident evanescent waves,
    a detector for detecting waves scattered by the object, and
    a processor for reconstructing the tomographic image by executing a prescribed mathematical algorithm with reference to the incident waves and the scattered waves to generate the tomographic image with subwavelength resolution.

9. The system as recited in claim 8 wherein the detector includes means for measuring scattering data from the object, said scattering data being related to a scattering potential of the object by an integral operator.

10. The system as recited in claim 9 wherein the processor includes means for reconstructing the tomographic image by executing the prescribed mathematical algorithm, determined with reference to the integral operator, on the scattering data, the prescribed mathematical algorithm further relating the scattering potential to the scattering data by another integral operator.

11. A system for generating a tomographic image of an object comprising:
- a source for illuminating the object with incident evanescent waves,
- a detector for measuring scattering data from the object wherein the scattering data is related to the object by an integral operator, and
- a processor for reconstructing the tomographic image by executing a prescribed mathematical algorithm, determined with reference to the integral operator, on the scattering data to generate the tomographic image with subwavelength resolution.

12. The system as recited in claim 11 wherein the scattering data is related to a scattering potential of the object by the integral operator, and wherein the processor includes means for reconstructing the tomographic image by executing the prescribed mathematical algorithm, determined with reference to the integral operator, on the scattering data, the prescribed mathematical algorithm further relating the scattering potential to the scattering data by another integral operator.

* * * * *